March 13, 1945. T. YOSHIOKA Plant Pat. 654
GARDENIA PLANT
Filed May 15, 1944
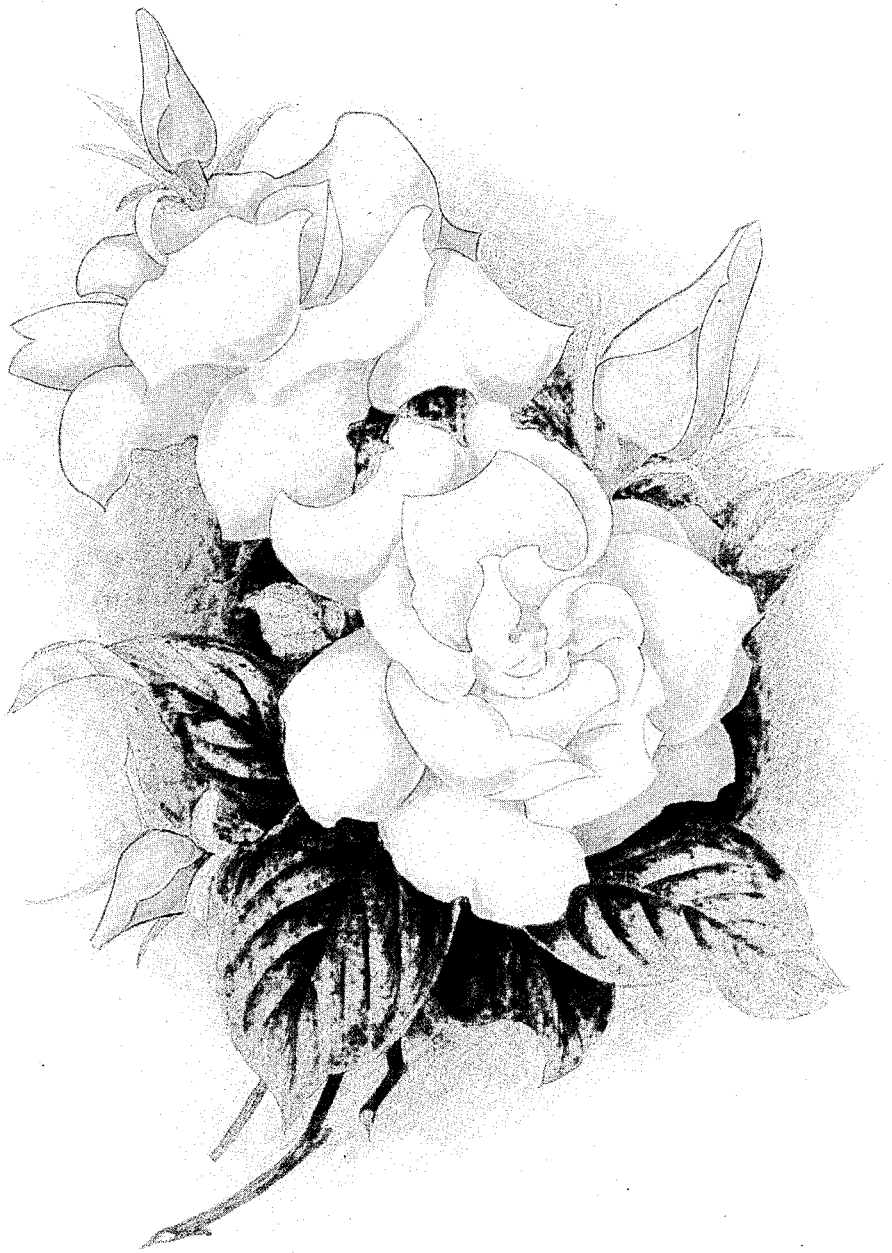
WITNESS
Addison E. Avery
Inventor,
TADAO YOSHIOKA, by
Rummler Rummler & Davis,
his Attorneys.

Patented Mar. 13, 1945

Plant Pat. 654

UNITED STATES PATENT OFFICE

654

GARDENIA PLANT

Tadao Yoshioka, Honolulu, Territory of Hawaii

Application May 15, 1944, Serial No. 535,678

1 Claim. (Cl. 47—60)

My discovery relates to a new and distinct variety of gardenia plant, the result of a definite effort to breed desirable characteristics for a pure white untinged flower, with a flowering period of practically the entire year. I began hybridization in 1938. This new variety has been reproduced by budding through several generations and its characteristics appear to be permanently fixed.

As a seed parent I took *Gardenia grandiflorum*, and by crossing it with its own pollen, reproduced a seedling in whose progeny the novel characteristics appeared and are perpetuated by asexual reproduction. The plant has not yet been reproduced for the market.

The main object of my invention was to produce a new and distinct type of vigorous and hardy gardenia plant having a flowering period practically the year around with the peak during March, April and May—earlier than other varieties—and having pleasing, desirable commercial qualities which have not previously existed in any known varieties. To my knowledge and belief it does not resemble any known variety. The ordinary layman has been able to distinguish this gardenia as a distinctly new type.

Distinguishing characteristics reside in its free and abundant blooming habit throughout the entire year; in the large untinted pure white blossoms, occurring on short, sturdy, erect stems, opening perfectly flat with the center always covered; and its long-lasting quality on the plant and as a cut flower.

The petals of the bloom are attached to one another in the corolla tube. Both petals and leaves are veined. The plant is an evergreen. The bud of my new variety is similar to "Hadley" variety.

Gardenia plants in Hawaii grow into huge bushes. The plant on which the gardenia in the illustration grew is more than six feet high and is about four feet across. The blossoms of my gardenia are of wax-like appearance, pure white with no tints or tinge of any color, and more substantial in texture when compared with the varieties known as "Hadley" and "Mystery," and different from "Hadley," "Mystery" and "Veitchii," the latter being a winter-flowering variety and difficult to handle. The foliage of my gardenia is dark green and glossy; that of the "Hadley" is black green; and "Mystery" is a dull yellow green. Up to the present time I have found that my plant is entirely free from the diseases which are common to gardenias under greenhouse conditions.

The blooms are flat when they open with the center always entirely covered. The central petals are grouped in a tightly rolled arrangement, thus forming a sort of hood over the pollen-bearing structures. The peduncle of the flower is short. One hundred percent of the blossoms so far have bloomed in such manner.

Generally, gardenia blooms do not keep well and bruise easily. In this respect my new gardenia is superior to the known varieties. It has a long-lasting quality and does not brown readily.

My gardenia has a pleasing fragrance and in this respect resembles "Veitchii."

The original paintings accompanying this application show the characteristic form and pure white color of the blooms, the grey tinting being artistic shading to represent the curvature of the petals.

The following is a detailed description of my new variety:

Parentage: Seedling.
- *Seed parent.*—*Gardenia grandiflorum.*
- *Pollen parent.*—Self.

Classification: *Gardenia grandiflorum.*

*Flower*

Blooming habit: Recurrent; extended blooming period during entire year; peak in March, April, and May.

Bud: Similar to "Hadley."
- *Size.*—2½ inches.
- *Form.*—Tapered.
- *Color.*—Green.
- *Sepals.*—2 inches.
- *Calyx.*—6 sepals.

Flower:
- *Size.*—4 inches.
- *Form.*—Open and flat with covered center.
- *Borne.*—Singly.
- *Petalage.*—36 in all; largest 2 x 1½ in.
- *Color.*—Pure white—no tinge of any color whatsoever.
- *Discoloration.*—Not easily discolored.
- *Texture.*—Good, firm, and leathery.
- *Weather tolerance.*—Resistant to wet or hot weather, and tolerates wet.
- *Persistence (hang on and dry).*—Persistent.
- *Fragrance.*—Good; equal or superior to other varieties.
- *Lasting quality.*—On plant—superior to others; as a cut flower—very good.
- *Appearance.*—Inside—white. Outside—white.
- *Disease resistance.*—No diseases under greenhouse conditions.

Genital organs:
- *Stamens, anthers.*—Length, ½ inch; number, 6; color, yellow. Arrangement—suspended.
- *Pollen.*—Color, yellow.
- *Styles.*—Number, 1; length, ¼ inch.
- *Stigma.*—Color, white.
- *Ovaries.*—1.

Fruit: Not fertile.

*Plant*

Form: Bush. Height, 6 feet.
Foliage: Evergreen.
*Quantity.*—Normal.
*Color.*—New foliage, dark green; glossy. Old foliage, dark green.
*Size leaf.*—2 x 4 inches.
*Texture.*—Firm.
*Shape.*—Oblong.

The color designations according to A Dictionary of Color, by Maerz and Paul, are as follows:

| Section | Color | Plate | Letter | Number |
|---|---|---|---|---|
| Body color of bloom | White | 17 | A | 1 |
| Pale shadows of bloom | | 17 | B | 1 |
| Deep shadows of bloom | | 20 | A | 1 |
| Bud | | 17 | J | 3 |
| Calyx | | 18 | L | 5 |
| Body color of leaf | | 20 | J | 10 |
| Dark sections of leaf | | 31 | A | 11 |
| Under side of leaf | | 17 | K | 5 |
| Stem | | 8 | E | 2 |

My new variety is different from "Mystery" and "Veitchii" because (*a*) Mystery has more pointed leaves; has shorter calyx; flower does not open flat and shows the center of flower; has less petals; does not keep so well; produces generally during summer months. (*b*) Veitchii is rather more difficult to handle as the young plants must be propagated from thoroughly healthy ones, must have well-prepared soil with exact temperatures of heat and cold, the atmosphere must be rather close in the propagating house for a stated period and must have proper shade.

I claim:

The new and distinct variety of gardenia plant as herein shown and described, characterized particularly by its free, abundant blooming habit during the entire year; its glossy, dark green foliage with oblong leaves; its large, pure white, untinged blossoms, each bloom having an exceptionally large number of petals; its blooms opening flat at the base with the center deep and always covered by petals; the long-lasting quality of its blooms on the plant and as cut flowers with substantially no discoloration; and its resistance to disease.

TADAO YOSHIOKA.